United States Patent [19]

Steiner et al.

[11] Patent Number: 5,512,584
[45] Date of Patent: Apr. 30, 1996

[54] 1,3,4-TRISUBSTITUTED PIPERIDINE DERIVATIVES, THE PREPARATION AND USE THEREOF

[75] Inventors: Gerd Steiner, Kirchheim; Liliane Unger, Ludwigshafen; Hans P. Hofmann, Limburgerhof; Hans-Juergen Teschendorf, Dudenhofen; Berthold Behl, Ludwigshafen; Rudolf Binder, Worms, all of Germany

[73] Assignee: BASF Aktiengesellschaft, Ludwigshafen, Germany

[21] Appl. No.: 331,872

[22] Filed: Nov. 1, 1994

Related U.S. Application Data

[63] Continuation of Ser. No. 133,123, filed as PCT/EP92/00765, Apr. 4, 1992.

[30] Foreign Application Priority Data

Apr. 16, 1991 [DE] Germany .................. 41 12 353.0

[51] Int. Cl.⁶ .................. A61K 31/445; C07D 211/22
[52] U.S. Cl. .................. 514/330; 514/317; 514/326; 514/327; 546/212; 546/217; 546/237; 546/239; 546/240; 546/280; 546/340; 546/344
[58] Field of Search .................. 546/212, 217, 546/237, 239, 240, 280, 340, 344; 514/317, 326, 330, 327

[56] References Cited

U.S. PATENT DOCUMENTS

| | | | |
|---|---|---|---|
| 3,080,372 | 3/1963 | Janssen | 514/317 |
| 3,591,593 | 7/1971 | Thiele | 514/327 |
| 3,912,743 | 10/1975 | Christensen | 514/317 |
| 4,605,655 | 8/1986 | Yevich et al. | 514/252 |
| 4,711,899 | 12/1987 | Gaudilliere | 514/330 |

FOREIGN PATENT DOCUMENTS 410114  1/1991  European Pat. Off. .

*Primary Examiner*—Ceila Chang
*Attorney, Agent, or Firm*—Keil & Weinkauf

[57] ABSTRACT

Compounds of the formula

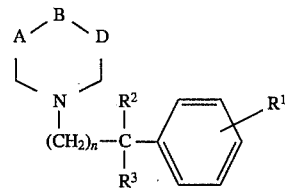

where A-B-D, $R^1$, $R^2$ and $R^3$ have the meanings stated in the description, and their preparation are described. The compounds are suitable for controlling diseases.

9 Claims, No Drawings

1,3,4-TRISUBSTITUTED PIPERIDINE DERIVATIVES, THE PREPARATION AND USE THEREOF

This is a Continuation U.S. Ser. No. 08/133,123 filed Oct. 13, 1993, which is a 371 of PCT/EP92/00765, filed Apr. 4, 1992.

The present invention relates to 1,3,4-trisubstituted piperidine derivatives, to a process for their preparation and to their use as drugs.

It is known that butyrophenone derivatives with basic substituents have neuroleptic and cerebroprotective effects (U.S. Pat. No. 4,605,655, EP 410 114). It appears in this connection that the observed affinities for σ receptors are particularly important.

We have now found that 1,3,4-trisubstituted piperidine derivatives of the formula I

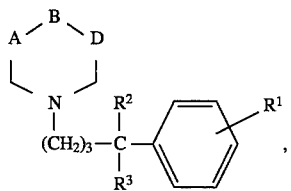

where $R^1$ is hydrogen, fluorine, chlorine or bromine, $R^2$ is hydroxyl, or phenyl which is unsubstituted or substituted by fluorine, chlorine or bromine, $R^3$ is hydrogen, or $R^2$ and $R^3$ together are oxygen, and A-B-D is

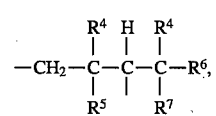

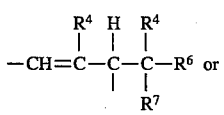

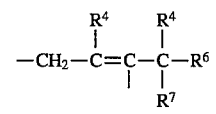

where $R^4$ is $C_{1-3}$-alkyl or is phenyl or thienyl which can be substituted by fluorine or chlorine, $R^5$ is hydrogen or hydroxyl, $R^6$ is hydrogen, $R^7$ is hydroxyl, or $R^6$ and $R^7$ together are oxygen, and their salts with physiologically tolerated acids have valuable pharmacological properties.

$R^1$ to $R^7$ and n in the formula I preferably have the following meanings:

$R^1$: hydrogen, fluorine, chlorine $R^2$: hydroxyl, p-fluorophenyl $R^3$: hydrogen or together with $R^2$ oxygen $R^4$: methyl, ethyl, phenyl, p-fluorophenyl, 2-thienyl $R^5$: hydrogen, hydroxyl $R^6$: hydrogen $R^7$: hydroxyl or with $R^6$ oxygen.

The following compounds are particularly preferred:
1-(4-Fluorophenyl)-4-[4-hydroxy-trans-3-phenyl-(hydroxy)methyl-4-phenyl-1-piperidinyl]-1-butanone, 1-(4-fluorophenyl)-4-[trans-(3-phenyl-hydroxymethyl-4-phenyl)-4-hydroxy-piperidin-1-yl]-butan-1-ol, 1-(4-fluorophenyl)-4-(3-benzoyl-4-phenyl-$\Delta^4$-dehydropiperidin-1-yl)-butan-1-one, 1-(4-fluorophenyl)-4-(3-benzoyl-4-phenyl-$\Delta^3$-dehydropiperidin-1-yl)-butan-1-one, 1-(bis-4-fluorophenyl)-4-[trans-(3-phenyl-hydroxymethyl-4-phenyl)-4-hydroxy-piperidin-1-yl]-butane, 1-(4-fluorophenyl)-4-[trans-(3-p- fluorophenyl-hydroxymethyl-4-p-fluorophenyl- 4-hydroxy-piperidin-1-yl]-butan-1-one, 1-(4-fluorophenyl)-4-[trans-(3-p-fluorophenyl-hydroxymethyl-4-p-fluorophenyl-4- hydroxypiperidin-1-yl]-butan-1-ol, 1-(4-fluorophenyl)-4[trans-(3-acetyl-4-methyl)-4-hydroxy-piperidin-1-yl] -butan-1-one, 1-(4-fluorophenyl)-4-[trans-(3-acetyl-4-methyl)-4-hydroxy-piperidin-1-yl]-butan-1-ol, 1-( 4-fluorophenyl)-4-(3-acetyl-4-methyl-$\Delta^3$-dehydropiperidin- 1yl)-butan-1-one, 1-(4-fluorophenyl)-4-(3-acetyl-4-methyl-$\Delta^3$-dehydropiperidin- 1-yl)-butan-1-ol, 1-(bis-4-fluorophenyl)- 4- (3-acetyl-4-methyl-$\Delta^3$-dehydropiperidin- 1-yl)-butane.

The compounds of the formula I according to the invention can be prepared by reacting a compound of the formula II

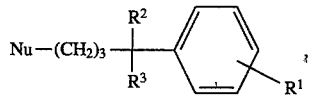

where $R^1$, $R^2$, $R^3$ and n have the stated meanings, and Nu is a nucleofugic leaving group, with a 3,4-disubstituted piperidine derivative of the formula III

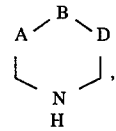

where A, B and D have the meanings stated for formula I, and converting the resulting compound where appropriate into the addition salt with a physiologically tolerated acid.

A suitable and preferred nucleofugic leaving group for Nu is halogen, especially bromine or chlorine.

The reaction is expediently carried out in the presence of an inert base such as triethylamine or potassium carbonate to trap acid in an inert solvent such as a cyclic saturated ether, especially tetrahydrofuran or dioxane, or an alkylbenzene such as toluene or xylene.

The reaction is usually carried out at from 80 to 150° C. and is generally complete within from 1 to 10 hours.

The products of the formula I can be converted by subsequent reactions as indicated in the examples.

These reactions comprise oxidations of the 3-hydroxymethylpiperidine structure ($R^7$=OH in formula I) to the corresponding carbonyl derivatives with Jones reagent (chromium(VI) oxide in 25% strength sulfuric acid), reduction of the 2-butanone moiety ($R^2$+$R^3$ =oxygen) to the corresponding 2-butanol derivative with sodium boranate, elimination of $H_2O$ from the 4-hydroxypiperidine moiety ($R^5$=OH) to give $\Delta^4$-dehydropiperidine derivative with concentrated sulfuric acid, and the base-catalyzed double-bond shift to give the $\Delta^3$-dehydropiperidine compound.

The compounds of the formula I according to the invention are usually obtained in the form of yellowish or yellow crystals and can be purified by recrystallization from the conventional organic solvents, preferably from a lower alcohol, such as ethanol, or by column chromatography.

The free 1,3,4-trisubstituted piperidine derivatives of the formula I can be converted in a conventional way into the addition salts with a physiologically tolerated acid, preferably by adding one equivalent of the appropriate acid to a solution. Examples of pharmaceutically tolerated acids are hydrochloric acid, phosphoric acid, sulfuric acid, methanesulfonic acid, sulfamic acid, maleic acid, fumaric acid, oxalic acid, tartaric acid and citric acid.

The compounds according to the invention have valuable pharmacological properties. They can be used as neuroleptics, antidepressants, sedatives, hypnotics or cerebroprotectives. It is possible for a plurality of the said properties to be combined in one compound according to the invention.

They are therefore suitable for the treatment of psychoses, preferably schizophrenia, and anxiety states, for the treatment and prevention of strokes or disturbances of cerebral function with an organic cause, and for the treatment of sleep disturbances.

The present invention accordingly also relates to a therapeutic composition which contains a compound of the formula I or its physiologically tolerated acid addition salt as active substance in addition to conventional carriers and diluents, and to the use of the novel copounds for controlling diseases.

The compounds according to the invention can be administered in a conventional way orally or parenterally, intravenously or intramuscularly.

The dosage depends on the age, condition and weight of the patient and on the mode of administration. As a rule, the daily dose of active substance is about 1–100 mg/kg of body weight on oral administration and 0.1–2 mg/kg of body weight on parenteral administration.

The novel compounds can be used in conventional solid or liquid pharmaceutical forms, e.g. as uncoated or (film-)coated tablets, capsules, powders, granules, suppositories, solutions, ointments, creams or sprays. These are produced in a conventional way. The active substances can for this purpose be processed with conventional pharmaceutical aids such as tablet binders, fillers, preservatives, tablet disintegrants, flow regulators, plasticizers, wetting agents, dispersants, emulsifiers, solvents, retardants, antioxidants and/or propellant gases (cf. H. Sucker et al.: Pharmazeutische Technologie, Thieme-Verlag, Stuttgart, 1978). The forms obtained in this way normally contain the active substance in an amount of from 0.1 to 99% by weight.

The substances of the formula II which are required as starting materials for synthesizing the novel compounds are known.

The substances of the formula III have not previously been described (but see DE 41 12 352). They are prepared, for example, by reacting 2 mole equivalents of an α,β-unsaturated ketone of the formula IV

    IV or a β-halo ketone of the formula V

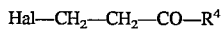    V, where $R^4$ has the abovementioned meanings, with an amine $H_2N—R^8$ where $R^8$ is benzyl which is unsubstituted or substituted by halogen, methoxy or nitro, or is allyl, in the presence of 1 mole equivalent of sodium hydroxide solution in methanol at 50° C. This reaction is usually diastereoselective to give the compound VI with diequatorial trans configuration with respect to $R^4$

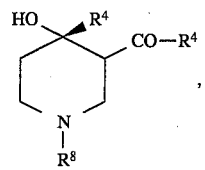    VI which can be converted by elimination of $R^8$ and, where appropriate, subsequent elimination of water and possible rearrangement and reduction as described above for the final products into the compounds of the formula III.

The following examples illustrate the invention:

EXAMPLE 1 a) Preparation of the starting material 4-hydroxytrans-3-phenyl(hydroxy)methyl-4-phenylpiperidine 600 g (1.62 mol) of trans-3-benzoyl-4-phenyl-4-hydroxy-1-benzylpiperidine in 1.4 l of ethyl acetate mixed with 1.4 l of methanol were catalytically hydrogenated with the addition of 20 g of palladium (10%) on carbon at 70° C. under a hydrogen pressure of 100 bar for 12 h. The mixture was filtered at 50° C. to remove catalyst, evaporated to dryness, taken up in 0.6 l of acetone and stirred while cooling. The precipitated product was filtered off with suction, the filtrate was concentrated, the residue was stirred in 300 ml of acetone again while cooling, and a second product fraction was filtered off with suction.

Yield: 345 g (75%) of the pure diastereomer of the product, melting point 167°–169° C.

b) Preparation of the final product 1-(4-fluorophenyl)-4-[4-hydroxy-trans-3-phenyl(hydroxy)methyl-4-phenyl-1-piperidinyl]-1-butanone 20.0 g (70.7 mmol) of 4-hydroxy-trans-3-phenyl-(hydroxy)methyl-4-phenylpiperidine in 210 ml of xylene were mixed with 26.7 ml (162 mmol) of ω-chloro-4-fluorobutyrophenone and with 18.8 g (136 mmol) of finely powdered potassium carbonate in addition to 1.0 g of potassium iodide and refluxed while stirring vigorously for 16 h. After cooling, 200 ml of toluene were added and the mixture was stirred vigorously while the pale solid precipitated. The crude product was filtered off with suction, washed with toluene and dried at 50° C. under reduced pressure. The solid was then digested in 1 l of water at 50° C. and finally the product was filtered off with suction (melting point 182°–183° C.), yield: 22.6 g (72%).

The following can be prepared in a similar way:

2. 1-(4-Fluorophenyl)-4-[4-hydroxy-trans-3-phenyl(hydroxy)methyl-4-phenyl-1-piperidinyl]butane Alkylating reagent: 1-(p-fluorophenyl)-4-chlorobutane 3. 1-Phenyl-4-[4-hydroxy-trans-3-phenyl(hydroxy)methyl-4-phenyl-1-piperidinyl]-1-butanone, Melting point 173°–175° C.

4. 1-Phenyl-4-[4-hydroxy-trans-3-phenyl(hydroxy)methyl- 4-phenyl-1-piperidinyl]butane 5.1-(4-Bromophenyl)-4-[4-hydroxy-trans-3-phenyl(hydroxy)methyl-4-phenyl-1-piperidinyl]-1-butanone, Melting point 186°–187° C.

EXAMPLE 6 a) Preparation of the starting material 4-Hydroxy-trans-3-p-fluorophenyl(hydroxy)methyl-4-p-fluorophenylpiperidine 30.0 g (67.6 mmol) of 4-hydroxy-1-benzyl-trans-3-p-fluorobenzoyl-4-p-fluorophenylpiperidine hydrochloride in 1 l of methanol were catalytically hydrogenated with the addition of 4.0 g of palladium (10%) on carbon at 50° C. for 8 h. After filtration and washing with methanol, the filtrate was evaporated to dryness. The residue was taken up in a mixture of 140 ml of methanol and 500 ml of water at 70° C., concentrated ammonia was added until the mixture was alkaline, and the precipitated product was filtered off with suction and washed thoroughly with water. Drying at 60° C. under reduced pressure resulted in 20.2 g (94%) of product of melting point 215°–217° C.

b) Preparation of the final product 1-(4-Fluorophenyl)-4-[4-hydroxy-trans-3-p-fluoro-phenyl(hydroxy)methyl-4-p-fluorophenyl-1piperidinyl]-1-butanone 20.0 g (63.0 mmol) of 4-hydroxy-trans-3-p-fluoro-phenyl(hydroxy)methyl-4-p-fluorophenylpiperidine in a mixture of 250 ml of toluene and 25 ml of dimethylformamide were mixed with 20.6 ml (125 mmol) of ω-chloro-4-fluorobutyrophenone and with finely powdered potassium carbonate in addition to 1.0 g of potassium iodide and refluxed while stirring vigorously for 8 h. After cooling, the mixture was evaporated in a rotary evaporator, the residue was taken up in a little dimethylformamide, and the solution was poured into vigorously stirred ice-water. The precipitated solid was filtered off with suction, thoroughly washed with water and recrystallized from ethanol to give 23.5 g (78%) of product of melting point 175°–177° C.

The following can be prepared in a similar way:

7. 1-(4-Fluorophenyl)-4-[4-hydroxy-trans-3-p-fluorophenyl(hydroxy)methyl-4-p-fluorophenyl-1-piperidinyl]butane, melting point 170°–171° C.

8. 1-Phenyl-4-[4-hydroxy-trans-3-p-fluorophenyl-(hydroxy)methyl-4-p-fluorophenyl-1-piperidinyl]-1-butanone 9. 1-Phenyl-4-[4-hydroxy-trans-3-p-fluorophenyl-(hydroxy)methyl-4-p-fluorophenyl-1-piperidinyl]-butane

EXAMPLE 10 a) Preparation of the starting material 4-hydroxy-cis-3-acetyl-4-methylpiperidine 20.1 g (81.0 mmol) of 4-hydroxy-1-benzyl-cis-3-acetyl-4-methylpiperidine in 700 ml of methanol were catalytically hydrogenated with the addition of 2.5 g of palladium (10%) on carbon at room temperature for 8 h. After filtration and washing with methanol, the filtrate was evaporated to dryness. 11.9 g (94%) of product were isolated, melting point 91°–93° C. The hydrochloride melts at 118°–199° C.

The trans isomer can be prepared in a similar way: decomposition above 133° C. (hydrochloride).

b) Preparation of the final product 1-(4-Fluorophenyl)-4-[4-hydroxy-cis-3-acetyl-4-methyl-1-piperidinyl)-1-butanone 20.5 g (131 mmol) of 4-hydroxy-cis-3-acetyl-4-methylpiperidine in a mixture of 250 ml of toluene and 25 ml of dimethylformamide were mixed with 21.4 ml (131 mmol) of ω-chloro-4-fluorobutyrophenone and with 18 g (131 mmol) of finely powdered potassium carbonate in addition to 1.0 g of potassium iodide and refluxed while stirring vigorously for 3 h. After cooling, the mixture was evaporated in a rotary evaporator, and the residue was partitioned between methylene chloride and water. The aqueous phase was extracted with methylene chloride, and then the organic phase was dried with sodium sulfate and evaporated. The crude product was purified by column chromatography (silica gel, methylene chloride/methanol 98/2). 9.5 g (22%) of product were isolated, decomposition above 90° C. (tartrate).

The following can be prepared in a similar way:

11. 1-(4-Fluorophenyl)-4-[4-hydroxy-trans-3-acetyl-4-methyl-1-piperidinyl]-1-butanone, Melting point 174°–175° C. (hydrochloride)

12. 1-(4-Fluorophenyl)-4-[4-hydroxy-cis-3-acetyl-4-methyl)-1-piperidinyl]-1-butanol, Alkylating reagent: 1-hydroxy-1-(p-fluorophenyl)-4-chlorobutane 13. 1-(4-Fluorophenyl)-4-[4-hydroxy-trans-3-acetyl-4-methyl-1-piperidinyl]-1-butanol, melting point 97°–99° C., Alkylating reagent: 1-hydroxy-1-(p-fluorophenyl)- 4-chlorobutane 14. 1-(4-Fluorophenyl)-4-[4-hydroxy-cis-3-acetyl-4-methyl-1-piperidinyl]butane, melting point 85°–88° C. (hydrochloride)

15. 1-(4-Fluorophenyl)-4-[4-hydroxy-trans-3-acetyl-4-methyl-1-piperidinyl]butane, melting point 105°–107° C. (hydrochloride)

16. 1-(4-Phenyl)-4-[4-hydroxy-cis-3-acetyl-4-methyl-1-piperidinyl]-1-butanone . 17. 1-(4-Phenyl)-4-[4-hydroxy-trans-3-acetyl-4-methyl-1-piperidinyl]- 1-butanone 18. 1-(4-Phenyl)-4-[4-hydroxy-cis-3-acetyl-4-methyl-1-piperidinyl ]butane 19. 1-(4-Phenyl)-4-[4-hydroxy-trans-3-acetyl-4-methyl-1-piperidinyl ]butane 20. 1- (4-Fluorophenyl)-4-[4-hydroxy-trans-3-propionyl-4-ethyl- 1-piperidinyl]-1-butanone

EXAMPLE 21

1,1-Bis (4-fluorophenyl)-4-[4-hydroxy-trans-3-phenyl(hydroxy) methyl-4-phenyl-1-piperidinyl]butane 22.8 g (80.6 mmol) of 4-hydroxy-trans-3-phenyl-(hydroxy)methyl-4-phenylpiperidine (Example 1a) in 400 ml of xylene mixed with 40 ml of DMF were mixed with 22.6 g (80.6 mmol) of 1,1-bis (4-fluorophenyl)-4-chlorobutane and with 18.6 g (132 mmol) of finely powdered potassium carbonate in addition to 0.3 g of potassium iodide and refluxed while stirring vigorously for 8 h. The mixture was cooled and then evaporated to dryness. The residue was dissolved in DMF, and the solution was poured into 2.5 l of vigorously stirred ice-water. After stirring for 1 hour, the precipitated solid was filtered off with suction to give 40.1 g (95%) of product of melting point 60°–162° C.

The following can be prepared in a similar way:

22. 1,1-Bis (4-fluorophenyl)-4-[4-hydroxy-trans- 390 3-p-fluorphenyl(hydroxy)methyl-4-p-fluorophenyl-1-piperidinyl]butane 23. 1,1-Bis(4-fluorophenyl)-4-[cis-3-acetyl-4-hydroxy-1-piperidinyl]butane, melting point 116°–119° C. (hydrochloride)

24. 1,1-Bis(4-fluorophenyl)-4-[trans-3-acetyl-4-hydroxy-1-piperidinyl]butane, melting point 93°–96° C. (hydrochloride)

EXAMPLE 25

1-(4-Fluorophenyl)-4-[4-hydroxy-trans-3-phenyl(hydroxy)-methyl-4-phenyl-1-piperidinyl]-1-butanol 5.0 g (11.6 mmol) of 1-(4-fluorophenyl)-4-[4-hydroxy-trans-3-phenyl(hydroxy)methyl-4-phenyl-1piperidinyl]-1-butanone (Example 1b) were dissolved in a mixture of 80 ml of methanol and 100 ml of tetrahydrofuran, and 0.6 g (16 mmol) of sodium boranate was added. The mixture was stirred at room temperature for 2 h and then concentrated in a rotary evaporator. The residue was partitioned between methylene chloride and water at pH 10, and the organic phase was dried with sodium sulfate and evaporated to give 4.6 g (88%) of product of melting point 90°–92° C. (decomposition).

The following can be prepared in a similar way:

26. 1-Phenyl-4-[4-hydroxy-trans-3-phenyl (hydroxy)methyl-4-phenyl- 1-piperidinyl]-1-butanol Melting point: 90°–92° C.
27. 1-(4-Fluorophenyl)-4-[4-hydroxy-trans-3-p-fluorophenyl(hydroxy)methyl-4-p-fluorophenyl-1-piperidinyl]1-butanol
28. 1-(4-Fluorophenyl)-4-[4-hydroxy-trans-3-p-fluorophenyl (hydroxy)methyl-4-p-fluorophenyl-1-piperidinyl]butane
29. 1-Phenyl-4-[4-hydroxy-trans-3-p-fluorophenyl (hydroxy)methyl-4-p-fluorophenyl-1-piperidinyl]-1-butanol
30. 1-(4-Fluorophenyl)-4-[4-hydroxy-cis-3-α-hydroxyethyl-4-methyl- 1-piperidinyl]-1-butanol
31. 1- (4-Fluorophenyl)-4- [4-hydroxy-trans-3-α-hydroxyethyl-4-methyl- 1-piperidinyl]- 1-butanol
32. 1-(4-Fluorophenyl)-4-[4-hydroxy-trans-3-αhydroxyethyl- 4-methyl-1-piperidinyl]butane
33. 1-(4-Bromophenyl)-4-[4-hydroxy-trans-3-phenyl(hydroxy)methyl-4-phenyl-1-piperidinyl]-1-butanol, Melting point 92°–93° C.
34. 1,1-Bis(4-fluorophenyl)-4-[4-hydroxy-cis-3-α-hydroxyethyl-4-methyl-1-piperidinyl]butane
35. 1,1-Bis(4-fluorophenyl)-4-[4-hydroxy-trans-3-α-hydroxyethyl-4-methyl-1-piperidinyl]butane

EXAMPLE 36

1-(4-Fluorophenyl)-4-[4-hydroxy-trans-3-benzoyl-4-phenyl-1-piperidinyl]-1-butanone 22.6 g (50.7 mmol) of 1-(4-fluorophenyl)-4-[4-hydroxy-trans-3-phenyl(hydroxy)methyl-4-phenyl-1-piperidinyl]-1-butanone (Example 1b) were suspended in 500 ml of acetone and then, while stirring vigorously, 21 ml (56 mmol) of Jones reagent were added dropwise. The temperature rose to 32° C. during this. The mixture was stirred at room temperature for 12 h and then evaporated in a rotary evaporator. The mixture was then poured into ice-water, methylene chloride was added, dilute sodium hydroxide solution was added until alkaline, and the precipitated chromium oxide was filtered off with suction. The aqueous phase was extracted with methylene chloride and then the organic phase was dried with sodium sulfate and concentrated to give 21.1 g (95%) of product of melting point 128°–130° C.

The following can be prepared in a similar way:

37. 1-(4-Fluorophenyl)-4-[4-hydroxy-trans-3-P-fluorobenzoyl-4-p-fluorophenyl-1-piperidinyl]-1-butanone, Melting point 111°–113° C.
38. 1-Phenyl-4-[4-hydroxy-trans-3-p-fluorobenzoyl-4-p-fluorophenyl-1-piperidinyl]-1-butanone

EXAMPLE 39

1,1-Bis(4-fluorophenyl)-4-[4-hydroxy-trans-3-benzoyl 4-phenyl-1-piperidinyl]butane 4.0 g (7.6 mmol) of 1,1-bis(4-fluorophenyl)-4-[4-hydroxy-trans- 3-phenyl (hydroxy) methyl-4-phenyl-1-piperidinyl ]butane (Example 21) were dissolved in 50 ml of glacial acetic acid and then, while stirring vigorously, 4.3 ml (11.4 mmol) of Jones reagent were added dropwise. The mixture was stirred at 60° C. for 12 h and then the solution was decanted off the precipitated chromium salts. The mixture was then poured into ice-water, methylene chloride was added, and sodium hydroxide solution was added until alkaline. The aqueous phase was extracted with methylene chloride and then the organic phase was dried with sodium sulfate and concentrated. The crude product was purified by column chromatography (silica gel, methylene chloride/methanol 98/2) to give 1.0 g (50%) of product (oil).

The following can be prepared in a similar way:

40. 1,1-Bis (4-fluorophenyl)-4-[4-hydroxy-trans-3-p-fluorobenzoyl-4-p-fluorophenyl- 1-piperidinyl ]butane

EXAMPLE 41 a) Preparation of the starting material
1. 4-Hydroxy-trans-3-benzoyl-4-phenylpiperidine 8 ml (21.4 mmol) of Jones reagent were added dropwise to 6.0 g (21.2 mmol) of 4-hydroxy-trans-3phenyl (hydroxy) methyl-4-phenylpiperidine (Example 1a) in 150 ml of acetone. The temperature rose to 30° C. during this. The mixture was stirred at room temperature for 1 h, and the solution was decanted off the precipitated chromium oxide and evaporated to half the volume in a rotary evaporator. The mixture was then poured into ice-water, dilute sodium hydroxide solution was added until alkaline, the mixture was extracted several times with methylene chloride, and the organic phase was dried with sodium sulfate and evaporated. 5.2 g (87%) of product were isolated and, after recrystallization from ethyl acetate, melted at 128°–129° C.

2. 3-Benzoyl-4 -phenyl-$\Delta^4$-dehydropiperidine 400 ml of methylene chloride and then 112.6 g (304 mmol) of 4-hydroxy-trans-3-benzoyl-4-phenyl-piperidine dissolved in 350 ml of methylene chloride were added dropwise to 186 g (1.9 mol) of concentrated sulfuric acid while cooling in ice to 0°–5° C. The mixture was stirred while cooling in ice for 2–3 h and then poured into ice-water, concentrated sodium hydroxide solution was added (to pH 10). The mixture was partitioned between methylene chloride and water, and the organic phase was dried over sodium sulfate and concentrated. The crude product was purified by column chromatography (silica gel, methylene chloride+5% methanol) to give a yield of 61 g (57%) of melting point 118°–119° C.)

b) Preparation of the final product
1-(4-Fluorophenyl)-4-[3-benzoyl-4-phenyl-$\Delta^4$-dehydro-1-piperidinyl]-1-butanone 15.4 g (59 mmol) of 3-benzoyl-4-phenyl-$\Delta^4$-dehydropiperidine in 90 ml of xylene were mixed with 11.5 ml (70 mmol) of e-chloro-4-fluorobutyrophenone and with 12.1 g (88 mmol) of finely powdered potassium carbonate together with 0.5 g of potassium iodide and refluxed while stirring vigorously for 15 h. The mixture was concentrated in a rotary evaporator and then the residue was partitioned between ice-water and methylene chloride, making alkaline with dilute sodium hydroxide solution. The aqueous phase was extracted with methylene chloride and then the organic phase was dried with sodium sulfate and concentrated. The crude product was purified by column chromatography (silica gel, methylene chloride/methanol 98/2) to give 5.2 g (21%) of product of melting point 89°–91° C. (hydrochloride).

The following can be prepared in a similar way:

42. 1-(4-Fluorophenyl)-4-[3-benzoyl-4-Phenyl-$\Delta^4$-dehydro-1-piperidinyl]-1-butanol

EXAMPLE 43

1-(4-Fluorophenyl)-4-[3-benzoyl-4-phenyl-$\Delta^4$-dehydro-1-piperidinyl]-1-butanone 100 ml of methylene chloride and then 10.0 g (22.4 mmol) of 1-(4-fluorophenyl)-4-[4-hydroxy-trans-3-benzoyl- 4-phenyl-1-piperidinyl]-1-butanone (Example 36) dissolved in 50 ml of methylene chloride were added dropwise to 18.0 ml (336 mmol) of concentrated sulfuric acid while cooling in ice to 0°–5° C. The mixture was stirred while cooling in ice for 2 h and then poured into ice-water, adjusted to pH 10 with concentrated sodium hydroxide solution and partitioned between methylene chloride and water, and the organic phase was dried over sodium sulfate and concentrated. The crude product was purified by column chromatography (silica gel, methylene chloride 99/1) to give a yield of 4.2 g (44%) of pale oil. The hydrochloride melts at 89°–91° C.

The following can be prepared in a similar way:

44. 1-(4-Fluorophenyl)-4- [3-benzoyl-4-phenyl-Δ4-dehydro-1-piperidinyl ]butane
45. 1-(4-Fluorophenyl)-4-[3-p-fluorobenzoyl-4-fluorophenyl-$\Delta^4$-dehydro- 1-piperidinyl ]- 1-butanone
46. 1- (4-Fluorophenyl)-4-[3-p-fluorobenzoyl-4-fluorophenyl-$\Delta^4$-dehydro- 1-piperidinyl ]butane
47. 1-Phenyl-4- [3-benzoyl-4-phenyl-Δ-dehydro-1-piperidinyl]-1-butanone
48. 1-Phenyl-4-[3-p-fluorobenzoyl-4-P-fluorophenyl-$\Delta^4$-dehydro-1-piperidinyl]- 1-butanone
49. 1,1-Bis(4-fluorophenyl)-4-[3-benzoyl-4-phenyl-$\Delta^4$-dehydro-1-piperidinyl]butane, Melting point 85°–87° C. (hydrochloride)
50. 1,1-Bis(4-fluorophenyl)-4-[3-p-fluorobenzoyl-4-p-fluorophenyl-$\Delta^4$-dehydro- 1-piperidinyl]butane

EXAMPLE 51

1-(4-Fluorophenyl)-4-[3-acetyl-4-methyl-$\Delta^3$-dehydro-1-piperidinyl]-1-butanone 200 ml of methylene chloride and then 22.0 g (68.5 mmol) of 1-(4-fluorophenyl)-4-[4-hydroxy-cis,trans-3-acetyl-4-methyl- 1-piperidinyl ]- 1-butanone (Example 10,11) dissolved in 100 ml of methylene chloride were added dropwise to 40 ml (747 mmol) of concentrated sulfuric acid while cooling in ice to 0°–5° C. The mixture was stirred while cooling in ice for 2 h and then at 30°–35° C. for 1 h, and was then poured into ice-water, adjusted to pH 10 with concentrated sodium hydroxide solution and partitioned between methylene chloride and water, and the organic phase was dried with sodium sulfate and concentrated. The crude product was purified by column chromatography (silica gel, methylene chloride 99/1) to yield 9.8 g (45%) of melting point 67°–70° C. (tartrate).

The following can be prepared in a similar way:

52. 1-(4-Fluorophenyl)-4-[3-acetyl-4-methyl-$\Delta^3$-dehydro-1-piperidinyl]butane
53. 1-Phenyl-4-[3-acetyl-4-methyl-$\Delta^3$-dehydro-1-piperidinyl]-1-butanone
54. 1-Phenyl-4-[3-acetyl-4-methyl-$\Delta^3$-dehydro-1-piperidinyl]butane

EXAMPLE 55

1-(4-Fluorophenyl)-4-[3-phenyl(hydroxy)methyl-4-phenyl-$\Delta^4$-dehydro-1-piperidinyl]-1-butanone 4.0 g (9.0 mmol) of 1-(4-fluorophenyl)-4-[3-benzoyl-4-phenyl-$\Delta^4$-dehydro-1-piperidinyl]-1-butanone (Example 41, 43) were suspended in 50 ml of methanol and, at 30° C., 0.34 g (9.0 mmol) of sodium boronate was slowly added. The mixture was stirred at room temperature for 2 h and then evaporated in a rotary evaporator. The residue was partitioned between methylene chloride and water at pH 10, and the organic phase was dried with sodium sulfate and concentrated to give 3.8 g (95%) of product of melting point 191°–192° C. (hydrochloride).

EXAMPLE 56 a) Preparation of the starting material
3-Benzoyl-4-phenyl-$\Delta^3$-dehydropiperidine 12.0 g (66 mmol) of 30% sodium methylate solution were added to 4.2 g (16.0 mmol) of 3-benzoyl-4- phenyl-$\Delta^4$-dehydropiperidine (Example 41a) in 60 ml of methanol, and the mixture was refluxed for 8 h and then stirred at room temperature overnight and evaporated to dryness in a rotary evaporator. The residue was poured into ice-water, the mixture was extracted several times with methylene chloride, and the organic phases were dried with sodium sulfate and evaporated. The crude product was purified by column chromatography (silica gel, methylene chloride+1% methanol) to yield 1.9 g (45%) of melting point 189°–192° C.

b) Preparation of the final product
1-(4-Fluorophenyl)-4-[3-benzoyl-4-phenyl-$\Delta^3$-dehydro-1-piperidinyl]-1-butanone 2.8 g (10.6 mmol) of 3-benzoyl-4-phenyl-$\Delta^3$-dehydropiperidine in 50 ml of xylene were mixed with 2.6 ml (15.4 mmol) of ω-chloro-4-fluorobutyrophenone and with 2.2 g (16 mmol) of finely powdered potassium carbonate together with 0.5 g of potassium iodide and refluxed while stirring vigorously for 13 h. The mixture was partitioned between methylene chloride and water, and the organic phase was dried with sodium sulfate and concentrated. The crude product was purified by column chromatography (silica gel, methylene chloride+5% methanol) to yield 1.4 g (31%) of product with melting point 171°–172° C.

The following can be prepared in a similar way:

57. 1-(4-Fluorophenyl)-4-[3-benzoyl-4-phenyl-$\Delta^3$-dehydro-1-piperidinyl]-1-butanol

EXAMPLE 58

1-(4-Fluorophenyl)-4-[3-benzoyl-4-phenyl-$\Delta^3$-dehydro-1-piperidinyl]-1-butanone 5.7 g (32 mmol) of 30% sodium methylate solution were added to 4.5 g (10.5 mmol) of 1-(4-fluorophenyl)-4-[3-benzoyl-4-phenyl-$\Delta^4$-dehydro-1-piperidinyl]-1-butanone (Example 41, 43) in 60 ml of methanol, and the mixture was refluxed for 1.5 h, then stirred at room temperature overnight and evaporated to dryness in a rotary evaporator. The residue was poured into ice-water, the mixture was partitioned between methylene chloride and water, the pH was adjusted to 10, and the organic phase was dried over sodium sulfate and concentrated. The crude product was purified by column chromatography (silica gel, methylene chloride+2.5% methanol) to yield 2.2 g (48%) of product whose maleate melts at 171°–172° C.

The following can be prepared in a similar way:

59. 1-(4-Fluorophenyl)-4-[3-benzoyl-4-phenyl-$\Delta^3$-dehydro1-piperidinyl]butane
60. 1-(4-Fluorophenyl)-4-[3-p-fluorobenzoyl-4-p-fluorophenyl-$\Delta^3$-dehydro-1-piperidinyl]-1-butanone, Melting point 211°–213° C. (hydrochloride)
61. 1-(4-Fluorophenyl)-4-[3-p-fluorobenzoyl-4-p-fluorophenyl-$\Delta^3$-dehydro-1-piperidinyl]butane
62. 1-Phenyl-4-[3-benzoyl-4-phenyl-$\Delta^3$-dehydro-1-piperidinyl]-1-butanone 63. 1-Phenyl-4-[3-p-fluorobenzoyl-4-p-fluorophenyl-$\Delta^3$-dehydro-1-piperidinyl]-1-butanone
64. 1,1-Bis(4-fluorophenyl)-4-[3-benzoyl-4-phenyl-$\Delta^3$-dehydro-1-piperidinyl]butane Melting point 85°–87° C. (hydrochloride)
65. 1,1-Bis(4-fluorophenyl)-4-[3-p-fluorobenzoyl-4-p-fluorophenyl-$\Delta^3$-dehydro-1-piperidinyl]butane.

EXAMPLE 66 a) Preparation of the starting material cis-3-phenyl(hydroxy)methyl-4-phenylpiperidine 7.8 g (22.1 mmol) of 3-benzoyl-4-phenyl-1-benzyl-$\Delta^4$-dehydropiperidine (prepared as in Example 41a) in 300 ml of ethanol were catalytically hydrogenated with the addition of 1.6 g of palladium (10%) on carbon at room temperature under atmospheric pressure for 48 h. The mixture was filtered to remove the catalyst, evaporated to dryness, taken up in 40 ml of acetone with heating, and cooled while stirring. The precipitated product was filtered off with suction and washed with acetone. Yield: 2.3 g (39%); the hydrochloride melts at 239°–240° C.

b) Preparation of the final product 1-(4-Fluorophenyl)-4-[cis-3-phenyl(hydroxy)methyl-4-phenyl-1-piperidinyl]-1-butanone 4.0 g (15.0 mmol) of cis-3-phenyl(hydroxy)methyl-4-phenylpiperidine in 50 ml of toluene were mixed with 3.8 ml (23 mmol) of ω-chloro-4-fluorobutyrophenone and with finely powdered potassium carbonate in addition to 1.0 g of potassium iodide and refluxed while stirring vigorously for 25 h. After cooling, the filtrate was concentrated, the residue was partitioned at pH 10 between methylene chloride and water, and the organic phase was dried and concentrated. The crude product was purified by column chromatography (silica gel, methylene chloride+5% methanol) to isolate 3.5 g (54%) of product of melting point 113°–114° C.

The following can be prepared in a similar way:

67. 1-(4-Fluorophenyl)-4-[cis-3-phenyl(hydroxy)methyl-4-phenyl-1-piperidinyl]butane
68. 1-(4-Fluorophenyl)-4-[cis-3-p-fluorophenyl(hydroxy)-methyl-4-p-fluorophenyl-1-piperidinyl]-1-butanone
69. 1-(4-Fluorophenyl)-4-[cis-3-acetyl-4-methyl-1-piperidinyl]-1-butanone
70. 1-(4-Fluorophenyl)-4-[cis-3-acetyl-4-methyl-1-piperidinyl]butane

We claim:
1. A 1,3,4-trisubstituted piperidine compound selected from formula I

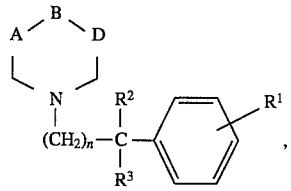

where $R^1$ is hydrogen, fluorine or chlorine,
$R^2$ is hydroxyl or p-fluorophenyl,
$R^3$ is hydrogen, or
$R^2$ and $R^3$ together are oxygen,
n is 1, 2 or 3, and
A-B-D is

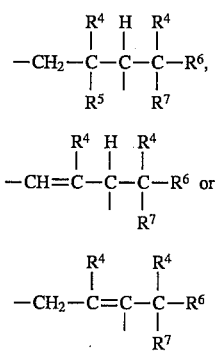

where $R^4$ is methyl, ethyl, phenyl, p-fluorophenyl or 2-thienyl,
$R^5$ is hydrogen or hydroxyl,
$R^6$ is hydrogen,
$R^7$ is hydroxyl, or
$R^6$ and $R^7$ together are oxygen with the proviso that when A-B-D is

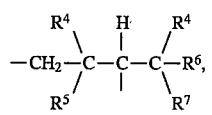

$R^4$ is methyl ethyl or 2-thienyl, and its salt with physiologically tolerated acid.

2. A 1,3,4-trisubstituted piperidine compound selected from formula I

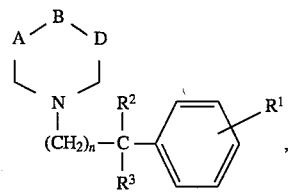

where $R^1$ is hydrogen or chlorine,
$R^2$ is hydroxyl or p-fluorophenyl,
$R^3$ is hydrogen, or
$R^2$ and $R^3$ together are oxygen,
n is 1, 2 or 3, and
A-B-D is

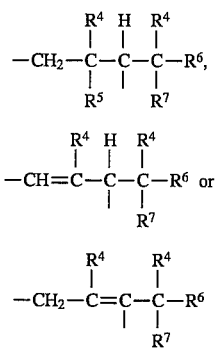

where $R^4$ is methyl, phenyl or p-fluorophenyl, $R^5$ is hydrogen or hydroxyl, $R^6$ is hydrogen, $R^7$ is hydroxyl, or $R^6$ and $R^7$ together are oxygen with the proviso that when A-B-D is,

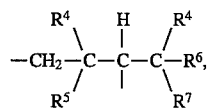

$R^4$ is methyl, ethyl or 2-thienyl and its salt with physiologically tolerated acid.

3. A compound selected from the group consisting of 1-(4-Fluorophenyl)-4-[4-hydroxy-trans-3-phenyl(hydroxy)methyl-4-phenyl-1-piperidinyl]-1-butanone, 1-(4-fluorophenyl)-4-[trans-(3-phenyl-hydroxymethyl-4-phenyl)-4-hydroxy-piperidin-1-yl]-butan-1-ol, 1-phenyl-3-[trans-(3-phenyl-hydroxymethyl-4-phenyl)-4-hydroxy-piperidin-1-yl]-propan-1-one, 1-(4-fluorophenyl)-4-(3-benzoyl-4-phenyl-$\Delta^4$-dehydro-piperidin-1-yl)-butan-1-one, 1-(4-fluorophenyl)- 4-(3-benzoyl-4-phenyl-$\Delta^3$-dehydro-piperidin-1-yl)-butan-1-one, 1-(bis-4-fluorophenyl)-4-[trans-(3-phenyl-hydroxymethyl-4-phenyl)-4-hydroxy-piperidin-1-yl] butane, 1-(4-fluorophenyl)-4-[trans-(3-p-fluorophenyl-hydroxymethyl-4-p-fluorophenyl-4-hydroxypiperidin-1-yl] butan-1-one, 1-(4-fluorophenyl)-4-[trans-(3-p-fluorophenyl-hydroxymethyl-4-p-fluorophenyl-4-hydroxypiperidin-1-yl]-butan-1-ol, 1-(4-fluorophenyl)-4-[trans-(3-acetyl-4-methyl)-4-hydroxy-piperidin-1-yl]-butan-1-one, 1-(4-fluorophenyl)-4-[trans-(3-acetyl-4-methyl)-4-hydroxypiperidin-1-yl]-butan-1-ol, 1-(4-fluorophenyl)-4-(3-acetyl-4-methyl-$\Delta^3$-dehydropiperidin-1-yl)-butan-1-one, 1-(4-fluorophenyl)-4-(3-acetyl-4-methyl-$\Delta^3$-dehydropiperidin-1-yl)-butan-1-ol, 1-(bis-4-fluorophenyl)-4-(3-acetyl-4-methyl-$\Delta^3$-dehydro-piperidin-1-yl)-butane.

4. A method for the treatment of strokes which comprises administering to a host in need thereof an effective amount of a 1,3,4-trisubstituted piperidine compound selected from formula I

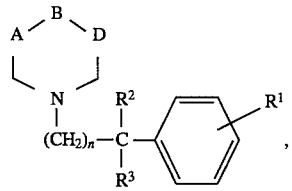

where $R^1$ is hydrogen, fluorine, chlorine or bromine, $R^2$ is hydrogen, hydroxyl, or phenyl which is unsubstituted or substituted by fluorine, chlorine or bromine, $R^3$ is hydrogen, or $R^2$ and $R^3$ together are oxygen, n is 1, 2 or 3, and A-B-D is

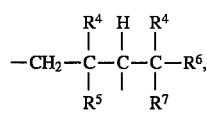

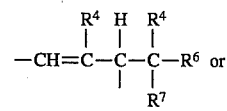

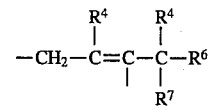

where $R^4$ is $C_{1-3}$-alkyl or is phenyl or thienyl which can be substituted by fluorine or chlorine, $R^5$ is hydrogen or hydroxyl, $R^6$ is hydrogen, $R^7$ is hydroxyl, or $R^6$ and $R^7$ together are oxygen, and n is 1, 2 or 3, and its salt with physiologically tolerated acid.

5. A method for the treatment of anxiety states which comprises administering to a host in need thereof an effective amount of a 1,3,4-trisubstituted piperidine compound selected from formula I

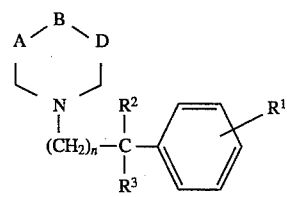

where $R^1$ is hydrogen, fluorine, chlorine or bromine, $R^2$ is hydrogen, hydroxyl, or phenyl which is unsubstituted or substituted by fluorine, chlorine or bromine, $R^3$ is hydrogen, or $R^2$ and $R^3$ together are oxygen, n is 1, 2 or 3, and A-B-D is

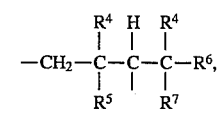

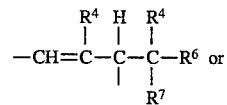

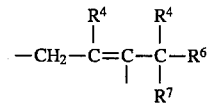

where $R^4$ is $C_{1-3}$-alkyl or is phenyl or thienyl which can be substituted by fluorine or chlorine, $R^5$ is hydrogen or hydroxyl, $R^6$ is hydrogen, $R^7$ is hydroxyl, or $R^6$ and $R^7$ together are oxygen, and n is 1, 2 or 3, and its salt with physiologically tolerated acid.

6. A method for the treatment of sleep disturbances which comprises administering to a host in need thereof an effective amount of a 1,3,4-trisubstituted piperidine compound selected from formula I

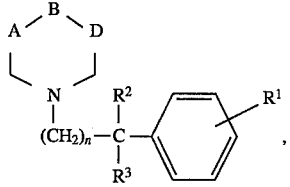

where $R^1$ is hydrogen, fluorine, chlorine or bromine, $R^2$ is hydrogen, hydroxyl, or phenyl which is unsubstituted or substituted by fluorine, chlorine or bromine, $R^3$ is hydrogen, or $R^2$ and $R^3$ together are oxygen, n is 1, 2 or 3, and A-B-D is

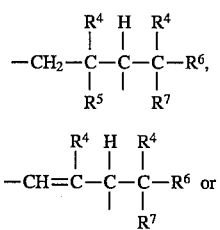

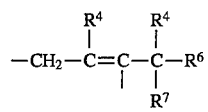

where $R^4$ is $C_{1-3}$-alkyl or is phenyl or thienyl which can be substituted by fluorine or chlorine, $R^5$ is hydrogen or hydroxyl, $R^6$ is hydrogen, $R^7$ is hydroxyl, or $R^6$ and $R^7$ together are oxygen, and n is 1, 2 or 3, and its salt with physiologically tolerated acid.

7. A method for the treatment of strokes which comprises administering to a host in need thereof an effective amount of the compound of claim 2.

8. A method for the treatment of anxiety states which comprise administering to a host in need thereof an effective amount of the compound of claim 2.

9. A method for the treatment of sleep disturbances which comprises administering to a host in need thereof an effective amount of the compound of claim 2.

* * * * *